United States Patent
Koike et al.

(10) Patent No.: US 11,912,638 B2
(45) Date of Patent: Feb. 27, 2024

(54) METHOD FOR PRODUCING CUMENE

(71) Applicant: Sumitomo Chemical Company, Limited, Tokyo (JP)

(72) Inventors: Hirofumi Koike, Sodegaura (JP); Tatsuro Uekusa, Ichihara (JP); Shoko Ikeda, Ichihara (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 17/633,744

(22) PCT Filed: Aug. 6, 2020

(86) PCT No.: PCT/JP2020/030207
§ 371 (c)(1),
(2) Date: Feb. 8, 2022

(87) PCT Pub. No.: WO2021/029324
PCT Pub. Date: Feb. 18, 2021

(65) Prior Publication Data
US 2022/0363611 A1    Nov. 17, 2022

(30) Foreign Application Priority Data

Aug. 9, 2019   (JP) .................... 2019-148080

(51) Int. Cl.
*C07C 1/24*     (2006.01)
*C07C 1/22*     (2006.01)

(52) U.S. Cl.
CPC . *C07C 1/24* (2013.01); *C07C 1/22* (2013.01)

(58) Field of Classification Search
CPC ................ C01C 1/22; C07C 1/24; C07C 5/01
See application file for complete search history.

(56) References Cited

U.S. PATENT DOCUMENTS

| | | | |
|---|---|---|---|
| 7,053,226 B2 | 5/2006 | Tsuji et al. | |
| 7,319,177 B2 * | 1/2008 | Tsuji | C07C 5/03 585/440 |
| 7,442,843 B2 * | 10/2008 | Suzuki | C07C 5/03 549/523 |
| 2004/0260134 A1 | 12/2004 | Tsuji et al. | |
| 2005/0054890 A1 | 3/2005 | Murray et al. | |
| 2006/0217566 A1 | 9/2006 | Suzuki et al. | |

FOREIGN PATENT DOCUMENTS

| | | |
|---|---|---|
| CN | 1616383 A | 5/2005 |
| CN | 102746100 A | 10/2012 |
| CN | 108929189 A | 12/2018 |
| JP | 2003-081886 A | 3/2003 |
| JP | 2003327563 A | 11/2003 |
| JP | 2004-203753 A | 7/2004 |
| JP | 2005-120076 A | 5/2005 |
| JP | 2009007294 A | 1/2009 |
| JP | 2009167130 A | 7/2009 |
| RU | 2340587 C2 | 12/2008 |
| WO | 2005030682 A1 | 4/2005 |

OTHER PUBLICATIONS

Int'l Search Report dated Sep. 24, 2020 in Int'l Application No. PCT/JP2020/030207.
Examination Report dated Sep. 30, 2021 in GC Application No. GC2020-40245.
International Preliminary Report on Patentability dated Feb. 17, 2022 in International Application No. PCT/JP2020/030207.
Office Action dated Jun. 14, 2023 in RU Application No. 2022105677.
Office Action dated Aug. 9, 2023 in IN Application No. 202247009905.
Extended European Search Report dated Jun. 20, 2023 in EP Application No. 20852278.9.
Office Action dated Nov. 2, 2023 in EP Application No. 20852278.9.

* cited by examiner

*Primary Examiner* — Sharon Pregler
(74) *Attorney, Agent, or Firm* — Panitch Schwarze Belisario & Nadel LLP

(57) ABSTRACT

A method for producing cumene involves subjecting cumyl alcohol to (a) hydrocracking reaction, or (b) dehydration and subsequent hydrogenation reaction, to obtain cumene. The method includes the following steps:
  (A): feeding a liquid containing cumene to a reactor loaded with a catalyst,
  (B): feeding hydrogen and a liquid containing cumyl alcohol to the reactor after the step (A).

14 Claims, No Drawings

METHOD FOR PRODUCING CUMENE

CROSS-REFERENCE TO RELATED APPLICATIONS

This application is a Section 371 of International Application No. PCT/JP2020/030207, filed Aug. 6, 2020, which was published in the Japanese language on Feb. 18, 2021 under International Publication No. WO 2021/029324 A1, which claims priority under 35 U.S.C. § 119(b) to Japanese Application No. 2019-148080, filed on Aug. 9, 2019 the disclosure of which is incorporated herein by reference in its entirety.

TECHNICAL FIELD

The present invention relates to a method for producing cumene.

BACKGROUND

A process involving hydrogenation reaction by bringing a liquid organic compound into contact with hydrogen in the presence of a catalyst is conventionally known.

It is known bringing hydrogen gas into contact with a catalyst at the start-up of such a process before a liquid organic compound and hydrogen are brought into contact with a catalyst and then bringing the liquid organic compound into contact the hydrogen with the catalyst.

For example, in Patent Literature 1, it is disclosed that, at the start-up of a process for hydrogenating dinitrile by bringing a liquid of aromatic dinitrile into contact with hydrogen in the presence of a catalyst, hydrogen is first brought into contact with a catalyst, follow by bringing the hydrogen and a liquid containing isophthalonitrile into contact with the catalyst.

CITATION LIST

Patent Literature

Patent Literature 1: Japanese Unexamined Patent Publication No. 2003-327563

SUMMARY

Technical Problem

As one of processes involving hydrogenation reaction by bringing a liquid organic compound into contact with hydrogen in the presence of a catalyst, there is a process for obtaining cumene, the process including subjecting liquid cumyl alcohol to (a) hydrocracking reaction, or (b) dehydration and subsequent hydrogenation reaction, in the presence of a catalyst. In the present specification, cumyl alcohol refers to 2-phenyl-2-propanol.

However, when the present inventors have examined, it has been found that when the above-mentioned method is applied at the start-up of such a process, the amount of isopropylcyclohexane produced, which is a reaction by-product, increases, which is problematic.

The present invention has been made in light of the above-mentioned problem, and an object thereof is to provide a method for producing cumene wherein the amount of isopropylcyclohexane produced, which is a by-product, is small.

Solution to Problem

A method for producing cumene according to the present invention is a method for obtaining cumene by subjecting cumyl alcohol to (a) hydrocracking reaction, or (b) dehydration and subsequent hydrogenation reaction, the method comprising the following steps A and B:
step A: feeding a liquid containing cumene to a reactor loaded with a catalyst, and
step B: feeding hydrogen and a liquid containing cumyl alcohol to the reactor after the step A.

Advantageous Effect of Invention

According to the present invention, there is provided a method for producing cumene wherein the amount of isopropylcyclohexane produced, which is a by-product, is small.

DESCRIPTION OF EMBODIMENTS (Method for Producing Cumene According to First Embodiment)

A method for producing cumene according to a first embodiment of the present invention will be described.

The method for producing cumene according to the first embodiment of the present invention is a method for producing cumene by subjecting cumyl alcohol to (a) hydrocracking reaction, or (b) dehydration and subsequent hydrogenation reaction, to obtain cumene. This method comprises the following steps A and B.
Step A: feeding a liquid containing cumene to a reactor loaded with a catalyst
Step B: feeding hydrogen and a liquid containing cumyl alcohol to the reactor after the step A
The present embodiment will be described in detail hereinafter.

Step A

In the step A, a liquid containing cumene is fed to a reactor. The concentration of cumene in the liquid in the step A can be 50% by mass or more, 60% by mass or more, and 70% by mass or more. In one aspect, the concentration of cumene in the liquid can be 90% by mass or more, and is preferably 95% by mass or more, more preferably 98% by mass or more, and further preferably 99% by mass or more. The concentration of cumene in the liquid may be 100% by mass.

The liquid may contain cumyl alcohol. In one aspect, the concentration of cumyl alcohol in the liquid can be 50% by mass or less, 40% by mass or less, or 30% by mass or less. In one aspect, the concentration of cumyl alcohol in the liquid can be 10% by mass or less, is preferably 5% by mass or less, more preferably 2% by mass or less, and further preferably 1% by mass or less.

It is suitable to raise the temperature of the catalyst in the reactor during the step A. It is suitable to raise the temperature of the catalyst in the reactor so that the temperature is in the below-mentioned reaction temperature range at the end of the step A.

Hydrogen is not usually fed to the reactor at the start of the step A. The molar ratio of hydrogen/(cumene+cumyl alcohol) at the start of the step A is preferably 1/25 or less, more preferably 1/30 or less, and further preferably 1/40 or less.

In one aspect, while the step A is performed, the molar ratio of hydrogen/(cumene+cumyl alcohol) is preferably 1/25 or less, more preferably 1/30 or less, and further preferably 1/40 or less. In one aspect, while the step A is performed, hydrogen is not fed to the reactor.

Step B

In the step B, hydrogen and a liquid containing cumyl alcohol are fed to the reactor.

Although the concentration B1 of cumyl alcohol in the liquid in the step B is not limited, it is preferable that the concentration B1 be 10% by mass or more, and the concentration B1 may be 20% by mass or more, and although the maximum is not limited, the concentration B1 can be 60% by mass or less, 50% by mass or less, or 40% by mass or less.

The liquid may contain cumene. In one aspect, the concentration of cumene in the liquid can be 90% by mass or less, 80% by mass or less, or 70% by mass or less. In one aspect, the concentration of cumen in the liquid can be 50% by mass or more, 60% by mass or more, or 70% by mass or more.

The concentration B1 of cumyl alcohol in the liquid in the step B and the concentration of cumyl alcohol in the liquid in the step A are independent. The concentration B1 of cumyl alcohol in the liquid in the step B and the concentration of cumyl alcohol in the liquid in the step A may be the same.

In the step B, it is suitable to maintain the temperature of the reactor in the below-mentioned reaction temperature range. When the temperature of the reactor is not raised in the step A, it is suitable to raise the temperature of the reactor in the below-mentioned reaction temperature range in the step B.

The amount of the liquid fed to the reactor in the step B can be suitably set according to the type and the amount of the catalyst.

In the step B, hydrogen is fed to the reactor with the liquid. The amount of hydrogen will be mentioned below.

In the step B, cumyl alcohol in the liquid containing cumyl alcohol is converted into cumene by (a) hydrocracking reaction, or (b) dehydration and subsequent hydrogenation reaction.

Catalyst and Conditions in Hydrocracking Reaction

Then, a catalyst and conditions when cumyl alcohol is subjected to (a) hydrocracking reaction to obtain cumene will be described.

In the case of hydrocracking reaction, a liquid containing cumene is obtained by bringing hydrogen and the liquid containing cumyl alcohol into contact with the catalyst to react the cumyl alcohol and the hydrogen in the reactor.

Examples of the catalyst used in hydrocracking reaction (hereinafter occasionally described as a "hydrocracking catalyst") include catalysts containing a metal of Group 9, 10 11 or 12 in the periodic table, and specific examples of the catalyst include catalysts containing cobalt, catalysts containing nickel, catalysts containing palladium, catalysts containing copper, and catalysts containing zinc. The catalysts containing nickel, the catalysts containing palladium, or the catalysts containing copper are preferable in view of suppressing the production of by-products. Examples of the catalysts containing nickel include nickel, nickel-alumina, nickel-silica and nickel-carbon; examples of the catalysts containing palladium include palladium-alumina, palladium-silica and palladium-carbon; and examples of the catalysts containing copper include copper, Raney copper, copper-chromium, copper-zinc, copper-chromium-zinc, copper-silica and copper-alumina.

The reactor used in hydrocracking reaction contains any one or a combination of a plurality of the above-mentioned catalysts. The reactor can be in the form of a slurry bed or a fixed bed. It is preferable to use a fixed bed in large-scale industrial operation. It is preferable to perform the reaction by a continuous method.

The amount of hydrogen consumed in hydrocracking reaction is equal to the number of moles of cumyl alcohol. However, since hydrogen-consuming components other than cumyl alcohol are also usually contained in the raw material liquid, it is suitable to feed excess hydrogen over the stoichiometric amount in view of securing the conversion rate of cumyl alcohol. As the partial pressure of hydrogen is increased, the reaction proceeds more rapidly. Therefore, the molar ratio of hydrogen/cumyl alcohol is usually adjusted to 1/1 to 20/1, is preferably 1/1 to 10/1, and is more preferably 1/1 to 5/1. The molar ratio of hydrogen/ (cumene+cumyl alcohol) is usually 1/25 or more. The molar ratio may be more than 1/25.

Excess hydrogen which remains after the hydrocracking reaction can also be separated from the reaction liquid, then recycled and used. Although the hydrocracking reaction temperature is usually 0 to 500° C., 50 to 450° C. is preferable, and 150 to 300° C. is more preferable. The hydrocracking reaction pressure is usually 100 to 10000 kPa-G, preferably 500 to 4000 kPa-G, and more preferably 1000 to 2000 kPa-G.

The conversion rate of cumyl alcohol when the hydrocracking reaction is applied is usually 90% or more.

Catalyst and conditions when dehydration reaction followed by hydrogenation reaction are performed Then, a catalyst and conditions when cumyl alcohol is subjected to (b) dehydration and subsequent hydrogenation reaction to obtain cumene will be described.

In this case, cumyl alcohol in the liquid is brought into contact with a catalyst in a reactor to obtain a liquid containing α-methylstyrene by the dehydration reaction of cumyl alcohol, and then, hydrogen and the liquid containing α-methylstyrene are brought into contact with a catalyst in a reactor to allow hydrogenation reaction between the α-methylstyrene and the hydrogen to thereby obtain a liquid containing cumene.

In the present aspect, the step of dehydrating cumyl alcohol in a liquid to obtain a liquid containing α-methylstyrene may be referred to as a "dehydration step", and the step of subjecting hydrogen and the liquid containing the α-methylstyrene in the liquid to hydrogenation reaction to obtain a liquid containing cumene may be referred to as a "hydrogenation step".

Examples of the catalyst used in the dehydration step (hereinafter occasionally described as a "dehydration catalyst") include homogeneous acid catalysts such as sulfuric acid, phosphoric acid and p-toluenesulfonic acid; and solid acid catalysts such as activated alumina, titania, zirconia, silica-alumina and zeolites. It is preferable to perform the dehydration step in the presence of a solid acid catalyst, and it is more preferable to use activated alumina, in view of improving reaction efficiency.

The dehydration reaction in the dehydration step is usually performed by bringing the liquid containing cumyl alcohol into contact with the dehydration catalyst in the reactor. Since dehydration reaction is followed by hydrogenation reaction in a hydrogenation step, the liquid containing cumyl alcohol may be brought into contact with the dehydration catalyst in the presence of hydrogen. The dehydration reaction temperature is usually 50 to 450° C., and preferably 150 to 300° C. The dehydration reaction pressure is usually 10 to 10000 kPa-G.

Examples of the catalyst used in the hydrogenation step (hereinafter occasionally referred to as a "hydrogenation catalyst") include catalysts containing a metal of Group 10 or 11 in the periodic table, and specific examples of the catalyst include catalysts containing nickel, catalysts containing palladium, catalysts containing platinum, and catalysts containing copper. The catalysts containing nickel, the catalysts containing palladium, and the catalysts containing copper are preferable from in view of suppressing the nucleus hydrogenation reaction of an aromatic ring, and high yield. As the catalysts containing nickel, nickel, nickel-alumina, nickel-silica and nickel-carbon are preferable; as the catalysts contains palladium, palladium-alumina, palladium silica and palladium-carbon are preferable; and as the catalysts containing copper, copper, Raney copper, copper-chromium, copper-zinc, copper-chromium-zinc, copper-silica and copper-alumina are preferable. These catalysts can be used alone or in combination of two or more.

The hydrogenation step is performed by bringing hydrogen and the liquid containing α-methylstyrene into contact with the hydrogenation catalyst in the reactor. Hydrogenation reaction follows the above-mentioned dehydration reaction, and some of water produced in the dehydration reaction may be separated by oil-water separation or the like, or water may be brought together with α-methylstyrene into contact with the hydrogenation catalyst without separation, in this aspect.

The amount of hydrogen consumed in the hydrogenation reaction is equal to the number of moles of α-methylstyrene. However, since hydrogen-consuming components other than α-methylstyrene are also usually contained in the raw material liquid, it is suitable to feed excess hydrogen over the stoichiometric amount in view of securing the conversion rate of α-methylstyrene. As the partial pressure of hydrogen is increased, the reaction proceeds more rapidly. Therefore, the molar ratio of hydrogen/α-methylstyrene is usually adjusted to 1/1 to 20/1, is preferably 1/1 to 10/1, and is more preferably 1/1 to 5/1. Excessive hydrogen which remains after the hydrogenation reaction can also be separated from the reaction liquid, then recycled and used. The molar ratio of hydrogen/(cumene+cumyl alcohol) is usually 1/25 or more. In the case of the (b), the amount of substance of "hydrogen" in the molar ratio is the amount of substance of hydrogen subjected to the hydrogenation reaction, and the amount of substance of "cumene+cumyl alcohol" is the total amount of substance of cumene and cumyl alcohol in the liquid subjected to dehydration reaction. The molar ratio may be more than 1/25.

Although the hydrogenation reaction temperature is usually 0 to 500° C., 30 to 400° C. is preferable, and 50 to 300° C. is more preferable. The hydrogenation reaction pressure is usually 100 to 10000 kPa-G.

The dehydration reaction and the subsequent hydrogenation reaction may be performed in a reactor that contains the dehydration catalyst and the hydrogenation catalyst sequentially from the upstream side in one container, a reactor that contains a catalyst obtained by physically mixing the dehydration catalyst and the hydrogenation catalyst in one container, a reactor that contains the hydrogenation catalyst supported on the dehydration catalyst in one container, or a reactor in which a container containing the dehydration catalyst and a container containing the hydrogenation catalyst are connected through a line in series sequentially from the upstream side.

The state of the contact between the catalyst and the liquid in the container can be in the form of a slurry bed or a fixed bed. It is preferable to use a fixed bed in large-scale industrial operation. In the present embodiment, the dehydration reaction and the subsequent hydrogenation reaction are performed by a continuous method.

According to a method according to the present embodiment, the amount of by-products, especially isopropylcyclohexane, in the reaction mixture can be reduced, and the selectivity from cumyl alcohol to cumene can be increased.

Method for Producing Propylene Oxide

The above-mentioned method for producing cumene is suitably applied to a step of producing cumene in the below-mentioned method for producing propylene oxide.

Specifically, the production of propylene oxide according to an embodiment of the present invention comprises the following steps.

Oxidization step: a step of oxidizing cumene to obtain cumene hydroperoxide

Epoxidation step: a step of reacting the cumene hydroperoxide obtained in the oxidization step and propylene to obtain propylene oxide and cumyl alcohol.

Cumene production step: a step of converting the cumyl alcohol obtained in the above-mentioned epoxidation step into cumene using the above-mentioned method for producing cumene and recycling the obtained cumene to the oxidization step These steps will be described hereinafter.

Cumene in the oxidization step is usually oxidized by autoxidation with oxygen-containing gas such as air and oxygen concentrated air. This oxidation reaction may be performed without using an additive, or with using an additive such as alkali. The reaction temperature is usually 50 to 200° C., and the reaction pressure is usually between atmospheric pressure and 5 MPa.

Example of the additive include alkali metal hydroxides such as NaOH and KOH; alkaline-earth metal hydroxides; alkali metal carbonates such as $Na_2CO_3$ and $NaHCO_3$; ammonia; $(NH_4)_2CO_3$; and alkali metal ammonium carbonates.

It is preferable to perform the epoxidation step in the presence of a catalyst containing titanium-containing silicon oxide in view of obtaining target propylene oxide at a high yield and a high selectivity. It is preferable that the catalyst be the so-called Ti-silica catalyst, which contains Ti chemically bound to silicon oxide. Examples of the catalyst includes catalyst in which Ti compounds are supported on silica carriers, catalysts in which Ti compounds are compounded with silicon oxide by a coprecipitation method or a sol-gel method, or zeolite compounds containing Ti.

The epoxidation reaction is performed by bringing propylene and cumene hydroperoxide into contact with a catalyst. The reaction can be performed in the liquid phase using a solvent. The solvent should be a liquid at the temperature and pressure of the reaction, and should be substantially inactive to the reactants and the products. An example of a solvent is cumene.

The epoxidation reaction temperature is generally 0 to 200° C., and preferably 25 to 200° C. The pressure may be a pressure enough to maintain the reaction mixture in a liquid state. It is generally advantageous that the pressure be 100 to 10000 kPa.

The epoxidation reaction can be advantageously performed using a catalyst in the form of a slurry bed or a fixed bed. It is preferable to use a fixed bed in large-scale industrial operation. The epoxidation reaction can be performed by a batch method, a semi-continuous method or a continuous method.

The cumyl alcohol produced in the epoxidation reaction is fed to the above-mentioned method for producing cumene. A liquid containing cumyl alcohol after propylene oxide and unreacted propylene are collected from the reaction mixture obtained in the epoxidation reaction is usually fed to a cumene production step.

Cumene produced in the cumene production step is recycled to the oxidization step. The obtained cumene may be purified by distillation, water washing and the like before recycling to the oxidization step.

The liquid containing cumene in the step A may be any liquid as long as it is a liquid containing cumene.

The liquid containing cumene in the step A may be a liquid that has undergone the cumene production step or a liquid containing cumyl alcohol after propylene oxide and unreacted propylene are collected from the reaction mixture obtained in the epoxidation reaction. A liquid containing cumene produced in another plant may be used for the liquid containing cumene in step A. Moreover, the liquid containing cumene in the step A may be a mixture of the above-mentioned liquids containing cumene.

The liquid containing cumene in step A after passing through the above-mentioned reactor can also be circulated to the oxidization step, the epoxidation step and the cumene production step.

The liquid containing cumyl alcohol in step B may be any liquid as long as it is a liquid containing cumyl alcohol, and, for example, the liquid containing the cumyl alcohol obtained by reacting propylene with the cumene hydroperoxide obtained by oxidizing cumene can be used.

The method for producing cumene according to the present invention can be performed in (a) the case where the reaction in the cumene production step is stopped, and then resumed; or (p) the case where the cumene production step is started for the first time.

For example, in the method for producing propylene oxide, when the reaction is stopped in all the steps of the oxidization step, the epoxidation step and the cumene production step, the reaction can be started by the following methods.

(1) A liquid containing cumene is fed to a reactor for the oxidization step. However, oxidation reaction is not performed, and the liquid containing cumene fed to the reactor for the oxidization step is fed to the epoxidation step as it is.
(2) The liquid containing cumene and passing the reactor for the oxidization step is fed to a reactor for the epoxidation step. However, the epoxidation reaction is not performed, and the liquid containing cumene fed to the reactor for the epoxidation step is fed to the cumene production step as it is.
(3) The liquid containing cumene and passing the reactor for the epoxidation step is used as a liquid containing cumene in the step A, and the step A is performed.
(4) After (3), the oxidation reaction in the oxidization step and the epoxidation reaction in the epoxidation step are started, and the cumyl alcohol concentration in the liquid containing cumene and passing the reactor for the oxidization step and the reactor for the epoxidation step is increased. In this case, since the liquid containing cumene and passing the reactor for the oxidization step and the reactor for the epoxidation step and the liquid after propylene oxide and unreacted propylene are separated from the reaction mixture contain cumyl alcohol, the step B is performed using these liquids as the liquid containing the cumyl alcohol in the step B.

In such a case, "the liquid containing cumene" fed to the reactor for the oxidization step may be the same as "the liquid containing cumene" in the step A in the above-mentioned method for producing cumene.

As an example of the method for producing cumene in such a case, a second embodiment will be described hereinafter.

(Method for Producing Cumene According to Second Embodiment)

A method for producing cumene according to a second embodiment is a method for producing cumene by subjecting cumyl alcohol to (a) hydrocracking reaction, or (b) dehydration and subsequent hydrogenation reaction, to obtain cumene. This method comprises the following step A' and step B'.

Step A': a step of feeding a liquid containing cumene having a cumyl alcohol concentration of 5% by mass or less to a reactor loaded with a catalyst Step B': a step of feeding hydrogen and a liquid having a cumyl alcohol concentration of 10% by mass or more to the reactor after the step A'

The present embodiment will be described in detail hereinafter.

Step A'

In the step A', a liquid containing cumene having a cumyl alcohol concentration of 5% by mass or less is fed to a reactor. It is preferable that the cumyl alcohol concentration $C0$ in step A' be sufficiently low, and, for example, the concentration may be 4% by mass or less, 3% by mass or less, 2% by mass or less, 1% by mass or less, 0.5% by mass or less, or 0.1% by mass or less, or may be substantially 0.

An example of components other than cumyl alcohol in the liquid is cumene. Cumene can account for 90% by mass or more of components other than cumyl alcohol in the liquid, and cumene accounts for preferably 95% by mass or more, more preferably 98% by mass or more, and further preferably 99% by mass or more.

It is suitable that the temperature of the catalyst in the reactor be raised during the step A'. It is suitable that the temperature of the catalyst in the reactor be raised so that the temperature at the end of the step A' is in the range of reaction temperature described for the step B of the first embodiment.

After all the catalyst in the reactor is brought into contact with the liquid containing cumene having a cumyl alcohol concentration of 5% by mass or less, the feeding of hydrogen to a reactor in the step A' may be started.

Step B'

In the step B', hydrogen and a liquid having a cumyl alcohol concentration $C1$ of 10% by mass or more are fed to the reactor. In the step B', the temperature of the reactor is maintained in the range of the reaction temperature described for the step B of the first embodiment. When the temperature of the reactor is not raised in the step A', the temperature of the reactor is raised in the step B' in the range of the reaction temperature described for the step B of the first embodiment.

The cumyl alcohol concentration $C1$ may be 10% by mass or more, and the concentration $C1$ may be 20% by mass or more. The upper limit thereof is not limited, and the concentration $C1$ can be 60% by mass or less, 50% by mass or less, and 40% by mass or less.

The liquid may contain cumene. In one aspect, the concentration of cumene in the liquid can be 90% by mass or less, 80% by mass or less, or 70% by mass or less. In one aspect, the concentration of cumene in the liquid can be 40% by mass or more, 50% by mass or more, or 60% by mass or more.

The amount of the liquid fed to the reactor in the step B' can be suitably set according to the type and the amount of a catalyst.

Hydrogen is fed to the reactor with the liquid having a cumyl alcohol concentration of 10% by mass or more, in step B'. The amount of hydrogen can be set as described for the step B of the first embodiment. Hydrogen may be started to be fed to the reactor prior to the step B', for example at the start of the step A' or in the middle of the step A', in view of improvement in the reaction rate. Alternatively, hydrogen may be started to be fed at the start of the step B' or in the middle of the step B', for example. When hydrogen is started to be fed at the start of the step A' or in the middle of the step A' and the below-mentioned step X' is provided between the step A' and the step B', the feeding of hydrogen may be continued in the step X'.

It is suitable that hydrogen be fed at least when the cumyl alcohol concentration in the liquid is 1% by mass or more, in view of allowing cumyl alcohol to react efficiently.

The concentration of the cumyl alcohol in the liquid fed to the reactor may be increased rapidly from a C0 of 5% by mass or less to a C1 of 10% by mass or more between the A' step and the B' step. The second embodiment may include, between the step A' and the step B', a step X' of increasing the cumyl alcohol concentration in the liquid fed to the reactor from a concentration C0 of 5% by mass or less to a concentration C1 of 10% by mass or more gradually.

In the step X', it is suitable to maintain the temperature of the reactor in the range of the reaction temperature described for the step B of the first embodiment. When the temperature of the reactor is not raised in the step A', it is suitable to raise the temperature of the reactor in the step X' in the range of the reaction temperature described for the step B of the first embodiment.

The feeding of hydrogen to the reactor may be started in the step X'.

EXAMPLES

Example 1

A metallic reactor having an inner diameter of 14 mm (the metal reactor contained a sheath having an outer diameter of 3 mm and equipped with a thermometer therein) was loaded with a catalyst (catalyst mass: 3.0 g; the catalyst contained activated alumina and 0.05% by mass palladium). A fixed bed was used for a method for supporting the catalyst.

Liquid cumene was fed to the reactor to fill the reactor with the liquid cumene under the pressure of 0.9 MPa-G. Then, while nitrogen gas and liquid cumene were fed at 84 Nml/minute and at 24 g/hour, respectively, to the reactor under the same pressure, the reactor was heated with an electric furnace so that the temperature of the inlet portion of the catalyst layer reached 230° C. After the temperature of the inlet portion of the catalyst layer stabilized at 230° C., nitrogen gas was switched to hydrogen gas, and hydrogen gas was fed at 72 Nml/minute under the same pressure. At almost the same time as the switch to hydrogen gas, a cumyl alcohol solution (1) (cumyl alcohol concentration: 26% by mass, cumene concentration: 71% by mass, isopropylcyclohexane concentration: 0.03% by mass) was fed to the reactor at 24 g/hour as a raw material liquid instead of liquid cumene by the switch of the liquid feeding lines. The number of moles of hydrogen fed per unit time was 4.3 times the number of moles of cumyl alcohol fed per unit time.

The amount of the liquid (reaction liquid sample) discharged from the reactor during the time from 43 minutes to 73 minutes after the start of hydrogen gas feeding was 11.3 g, and the cumyl alcohol concentration in the reaction liquid was 0.0% by mass. The analysis results are shown in Table 1. The average temperature of the catalyst layer measured during collection of the reaction liquid was 232° C. It was presumed that it was at 103 minutes after the start of hydrogen feeding that the cumyl alcohol concentration in the reactor became steady state.

The amount of the liquid (reaction liquid sample) discharged from the reactor during the time from 103 to 133 minutes after the start of hydrogen gas feeding was 10.9 g, and when the reaction liquid was analyzed, the cumyl alcohol concentration was 0.1% by mass. The analysis results are shown in Table 1. The average temperature of the catalyst layer measured during collection of the reaction liquid was 232° C.

Example 2

The same reactor as in Example 1 was provided. A cumene solution (1) (cumene concentration: 71% by mass, cumyl alcohol concentration: 26% by mass, isopropylcyclohexane concentration: 0.03% by mass) was fed to the reactor to fill the reactor with the cumene solution (1) under the pressure of 0.9 MPa-G. Then, while nitrogen gas and the cumene solution (1) were fed at 84 Nml/minute and 24 g/hour, respectively, to the reactor under the same pressure, the reactor was heated so that the temperature of the inlet portion of the catalyst layer reached 230° C. After the temperature of the inlet portion of the catalyst layer stabilized at 230° C., nitrogen gas was switched to hydrogen gas, and hydrogen gas was fed at 72 Nml/minute under the same pressure. In Example 2, the raw material liquid is the cumene solution (1). The number of moles of hydrogen fed per unit time was 4.3 times the number of moles of cumyl alcohol fed per unit time.

The amount of the liquid (reaction liquid sample) discharged from the reactor during the time from 35 minutes to 60 minutes after the start of hydrogen gas feeding was 9.6 g. The cumyl alcohol concentration in the reaction liquid at the time point of 35 minutes after the start of hydrogen gas feeding was 1.7% by mass. The analysis results are shown in Table 1. The average catalyst temperature measured after collection of the reaction liquid was 233° C.

Example 3

The same reactor as in Example 1 was provided. A cumene solution (2) (cumene concentration: 46% by mass, cumyl alcohol concentration: 51% by mass, isopropylcyclohexane concentration: 0.03% by mass) was fed to the reactor to fill the reactor with the cumene solution (2) under the pressure of 0.9 MPa-G. Then, while nitrogen gas and the cumene solution (2) were fed at 84 Nml/minute and 24 g/hour, respectively, to the reactor under the same pressure, the reactor was heated so that the temperature of the inlet portion of the catalyst layer reached 230° C. After the temperature of the inlet portion of the catalyst layer stabilized at 230° C., nitrogen gas was switched to hydrogen gas, and hydrogen gas was fed at 72 Nml/minute under the same pressure. In Example 3, the raw material liquid is the cumene solution (2). The number of moles of hydrogen fed per unit time was 2.1 times the number of moles of cumyl alcohol fed per unit time.

The amount of the liquid (reaction liquid sample) discharged from the reactor during the time from 30 minutes to 60 minutes after the start of hydrogen gas feeding was 12.2 g. The cumyl alcohol concentration in the reaction liquid at the time point of 30 minutes after the start of hydrogen gas feeding was 10.8% by mass. The analysis results are shown in Table 1. The average catalyst temperature measured after collection of the reaction liquid was 235° C.

Comparative Example 1

The same reactor as in Example 1 was provided. While nitrogen gas was fed to the reactor, the reactor was heated until the temperature of the inlet portion of the catalyst layer reached 210° C., under the pressure of 0.9 MPa-G. After the temperature of the inlet portion of the catalyst layer stabilized at 210° C., nitrogen gas was switched to hydrogen gas, and hydrogen gas was fed at 72 Nml/minute under the same pressure. On this occasion, the temperature of the inlet portion of the catalyst layer rose to 223° C. Then, the reactor was heated so that the temperature of the inlet portion of the catalyst layer reached 230° C. under the same pressure. Then, a cumyl alcohol solution (1) (cumyl alcohol concentration: 26% by mass, cumene concentration: 71% by mass, isopropylcyclohexane concentration: 0.03% by mass) was fed to the reactor at 24 g/hour as a raw material liquid under the same pressure. The number of moles of hydrogen fed per unit time was 4.3 times the number of moles of cumyl alcohol fed per unit time.

The reaction liquid was discharged from the reactor 43 minutes after the start of hydrogen gas feeding. The amount of the liquid (reaction liquid sample) discharged from the reactor during the time from 43 minutes to 73 minutes after the start of hydrogen gas feeding was 12.0 g, and the cumyl alcohol concentration in the reaction liquid was 1.6% by mass. The analysis results are shown in Table 1. The average catalyst temperature measured during collection of the reaction liquid was 233° C.

Comparative Example 2

The temperature of the inlet portion of the catalyst layer is expected to rise to 240° C. under the following conditions: the same reactor as in Example 1 is provided; while nitrogen gas is fed to the reactor, the reactor is heated until the temperature of the inlet portion of the catalyst layer reaches 230° C.; nitrogen gas is then switched to hydrogen gas; and hydrogen gas was fed at 72 Nml/minute, under the pressure of 0.9 MPa-G.

The cumyl alcohol conversion rate and the isopropylcyclohexane selectivity in the following Table 1 were calculated by the following expressions.

Theoretical weight of liquid fed (g)=weight of sample collected×(cumyl alcohol concentration in raw material liquid×(molecular weight of cumyl alcohol/molecular weight of cumene)+(100−cumyl alcohol concentration in raw material liquid))/100

Number of moles of cumene in raw material liquid (mol)=theoretical weight of liquid fed×(cumene concentration in raw material liquid/molecular weight of cumene)/100

Number of moles of cumyl alcohol in raw material liquid (mol)=theoretical weight of liquid fed×(cumyl alcohol concentration in raw material liquid/molecular weight of cumyl alcohol)/100

Number of moles of isopropylcyclohexane in raw material liquid (mol)=theoretical weight of liquid fed×(isopropylcyclohexane concentration in raw material liquid/molecular weight of isopropylcyclohexane)/100

Number of moles of cumene in reaction liquid (mol)=weight of sample collected×(cumene concentration in reaction liquid/molecular weight of cumene)/100

Number of moles of cumyl alcohol in reaction liquid (mol)=weight of sample collected×(cumyl alcohol concentration in reaction liquid/molecular weight of cumyl alcohol)/100

Number of moles of isopropylcyclohexane in reaction liquid (mol)=weight of sample collected×(isopropylcyclohexane concentration in reaction liquid/molecular weight of isopropylcyclohexane)/100

Conversion rate of cumyl alcohol (%)=(number of moles of cumyl alcohol in raw material liquid−number of moles of cumyl alcohol in reaction liquid)/number of moles of cumyl alcohol in raw material liquid×100

Isopropylcyclohexane selectivity (%)=(number of moles of isopropylcyclohexane in reaction liquid−number of moles of isopropylcyclohexane in raw material liquid)/(number of moles of cumyl alcohol in raw material liquid−number of moles of cumyl alcohol in reaction liquid+number of moles of cumene in raw material liquid)×100

Cumene selectivity (%)=(number of moles of cumene in reaction liquid−number of moles of cumene in raw material liquid)/(number of moles of cumyl alcohol in raw material liquid−number of moles of cumyl alcohol in reaction liquid)×100

TABLE 1

|  | Example 1 | Example 2 | Example 3 | Comparative Example 1 |
|---|---|---|---|---|
| Cumene concentration of cumene solution (weight %) | 100 | 71 | 46 | — |
| Cumyl alcohol concentration in raw material liquid (weight %) | 26 | 26 | 51 | 26 |
| Sampling time | 43-73 min. | 103-133 min. | 35-60 min. | 30-60 min. | 43-73 min. |
| Cumyl alcohol concentration in reaction liquid (weight %) | 0.0 | 0.1 | 1.7 | 10.8 | 1.6 |
| Isopropylcyclohexane concentration in reaction liquid (weight %) | 2.6 | 2.3 | 0.9 | 0.1 | 4.4 |
| Weight of reaction liquid collected (g) | 11.3 | 10.9 | 9.6 | 12.2 | 12.0 |

TABLE 1-continued

|  | Example 1 | Example 2 | Example 3 | Comparative Example 1 |
|---|---|---|---|---|
| Conversion rate of cumyl alcohol (mol %) | 100.0 | 99.6 | 93.6 | 80.3 | 94.1 |
| Isopropylcyclohexane selectivity (mol %) | 2.4 | 2.2 | 0.8 | 0.1 | 4.3 |
| Cumene selectivity (mol%) | 90.8 | 88.2 | 98.4 | 87.2 | 70.6 |

The selectivity of isopropylcyclohexane, which is a by-product, was low in the Examples as compared with the Comparative Example.

The invention claimed is:

1. A method for producing cumene comprising the steps of:
(A) pretreating a catalyst by feeding a liquid stream containing cumene into a reactor containing the catalyst; and
(B) feeding hydrogen and a liquid stream containing cumyl alcohol to the reactor after the step (A);
wherein the step (B) comprises a hydrocracking reaction or a dehydration and subsequent hydrogenation reaction to obtain cumene.

2. The method according to claim 1, wherein the catalyst is a catalyst containing a metal of Group 10 and/or 11 in the periodic table.

3. The method according to claim 1, wherein the molar ratio of hydrogen/(cumene+cumyl alcohol) at the start of the step A is 1/25 or less.

4. The method according to claim 1, wherein while the step A is performed, the molar ratio of hydrogen/(cumene+cumyl alcohol) is 1/25 or less.

5. The method according to claim 1, wherein cumene is obtained by subjecting cumyl alcohol to (a) hydrocracking reaction.

6. The method according to claim 5, wherein the catalyst comprises at least one metal selected from the group consisting of cobalt, nickel, palladium, copper, and zinc.

7. The method according to claim 5, wherein the molar ratio of hydrogen/cumyl alcohol in hydrocracking reaction is 1/1 to 20/1.

8. The method according to claim 5, wherein temperature of the hydrocracking reaction is 0 to 500° C.

9. The method according to claim 5, wherein pressure of the hydrocracking reaction is 100 to 10000 kPa-G.

10. The method according to claim 1, wherein cumene is obtained by subjecting cumyl alcohol to (b) dehydration and subsequent hydrogenation reaction.

11. The method according to claim 10, wherein the catalyst used in the hydrogenation reaction comprises at least one metal selected from the group consisting of nickel, palladium, platinum, and copper.

12. The method according to claim 10, wherein the dehydration of cumyl alcohol produces α-methylstyrene and wherein the hydrogenation reaction comprises subjecting hydrogen and α-methylstyrene to hydrogenation, wherein the molar ratio of hydrogen/α-methylstyrene in the hydrogenation reaction is 1/1 to 20/1.

13. The method according to claim 10, wherein temperature of hydrogenation reaction is 0 to 500° C.

14. The method according to claim 10, wherein pressure of hydrogenation reaction is 100 to 10000 kPa-G.

* * * * *